United States Patent [19]

Hömberger et al.

[11] Patent Number: 5,071,869
[45] Date of Patent: Dec. 10, 1991

[54] 2-FLUOROCYCLOPROPYLACETIC ACID ESTERS, PROCESSES FOR THEIR PREPARATION AND THEIR USE AS PESTICIDES

[75] Inventors: Günter Hömberger; Arnim Köhn; Hartmut Joppien; Harald Von Keyserlingk, all of Berlin, Fed. Rep. of Germany

[73] Assignee: Schering Aktiengesellschaft, Fed. Rep. of Germany

[21] Appl. No.: 578,330

[22] Filed: Sep. 6, 1990

[30] Foreign Application Priority Data

Sep. 7, 1989 [DE] Fed. Rep. of Germany ....... 3930038

[51] Int. Cl.$^5$ .................. C07D 207/06; C07D 233/02; C07D 231/04; A61K 31/40
[52] U.S. Cl. ..................................... 514/423; 548/540
[58] Field of Search ......................... 548/540; 514/423

Primary Examiner—Mukund J. Shah
Assistant Examiner—Yogendran Gupta
Attorney, Agent, or Firm—Ostrolenk, Faber, Gerb & Soffen

[57] ABSTRACT

There are provided new 2-fluorocyclopropylacetic acid esters of general formula I

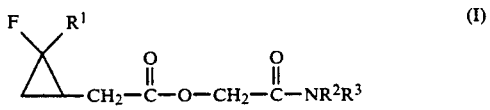

in which $R^1$, $R^2$ and $R^3$ have the meanings given in the description as well as processes for their preparation of the compounds of formula I.

The compounds of the invention can be used as pesticides, especially against insects and mites.

11 Claims, No Drawings

2-FLUOROCYCLOPROPYLACETIC ACID ESTERS, PROCESSES FOR THEIR PREPARATION AND THEIR USE AS PESTICIDES

The invention relates to new 2-fluorocyclopropylacetic acid esters, their preparation and their use as pesticides, especially against insects and mites.

It is already known that cyclopropane compounds possess acaricidal and insecticidal properties (EP 116 889).

The disadvantage of the known compounds however is that the insecticidal and acaricidal activity is not sufficiently high.

The object of the present invention is to provide new compounds that combat insects and mites better than compounds known for this purpose.

It has now been found that 2-fluorocyclopropylacetic acid esters of general formula I

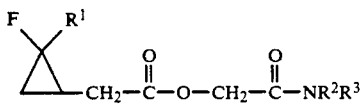

in which
$R^1$ is hydrogen, fluorine or chlorine, and
$R^2$ and $R^3$ independently of each other are hydrogen, $C_{1-20}$-alkyl, $C_{2-20}$-alkenyl, $C_{2-20}$-alkynyl, halo-$C_{1-10}$-alkyl, $C_{3-6}$-cycloalkyl, $C_{1-3}$-alkyl-$C_{3-6}$-cycloalkyl, $C_{3-6}$-cycloalkyl-$C_{1-6}$-alkyl, halo-$C_{3-6}$-cycloalkyl-$C_{1-6}$-alkyl, bicycloalkyl, aryl-$C_{1-6}$-alkyl, aryl-$C_{2-6}$-alkenyl, haloaryl-$C_{1-6}$-alkyl, $C_{1-4}$-alkylaryl- $C_{1-4}$-alkyl, haloaryl-$C_{2-6}$-alkenyl, halo-$C_{1-4}$-alkyl-aryl-$C_{1-6}$-alkyl, $C_{1-3}$-alkoxyaryl-$C_{1-6}$-alkyl, aryloxybenzyl, halophenyl(cyclopropyl)-$C_{1-3}$-alkyl, halo-phenoxy-$C_{1-6}$-alkyl, naphthyl-$C_{1-6}$-alkyl, aryl, optionally substituted by one or more of $C_{1-20}$-alkyl, halo-$C_{1-6}$-alkyl, $C_{1-16}$-alkoxy, halo-$C_{1-6}$-alkoxy, phenyl-$C_{1-6}$-alkyl, phenyl-$C_{1-6}$-alkoxy, $C_{3-10}$-cycloalkoxy, halo-$C_{3-10}$-cycloalkoxy, $C_{3-6}$-cycloalkylalkoxy, halo-$C_{3-6}$-cycloalkylalkoxy, $C_{2-6}$-alkenyloxy, halo-$C_{2-6}$-alkenyloxy, $C_{2-6}$-alkynyloxy, alkylsulphonyloxy, haloalkylsulphonyloxy, phenyl, halogen, amino, cyano, hydroxy, nitro, $C_{1-6}$-alkoxycarbonyl, $C_{1-6}$-alkoxy-carbonylmethyl, halo-$C_{1-6}$-alkoxycarbonyl, $C_{1-2}$-alkyldioxy, $C_{1-6}$-alkylthio, halo-$C_{3-6}$-cycloalkyl-alkylcarbonyloxy, $C_{1-6}$-alkylamino or di-$C_{1-6}$-alkyl-amino, or heteroaryl, optionally substituted by halogen, $C_{1-3}$-alkyl or halo-$C_{1-3}$-alkyl, or
$R^2$ and $R^3$ together with the nitrogen to which they are attached form a saturated, partially saturated or unsaturated heterocyclic ring,
have a better insecticidal and acaricidal activity in comparison with known compounds.

The term "alkyl" includes straight and branched carbon chains.

The term "alkenyl" includes straight and branched carbon chains that can contain one or more double bonds.

The term "alkynyl" includes straight and branched carbon chains that can contain one or more triple bonds.

The term "aryl" means one to three ringed aromatic groups, such as phenyl, naphthyl or phenanthryl.

The term "heteroaryl" means a 5- or 6-membered ring that contains one or more nitrogen, oxygen or sulphur atoms that can be saturated or partially saturated and can optionally carry a fused benzo ring, eg pyridine, thiazole or chromene.

The term "halogen" means fluorine, chlorine, bromine or iodine. Where a group is substituted by halogen this means that one or more hydrogen atoms of the group are replaced by halogen.

The term "heterocyclic ring" includes rings such as pyrrolidino, piperidino, tetrahydropyridino, piperazino or perhydroazepino.

Particularly preferred compounds are those in which
$R^1$ is fluorine or chlorine, and
$R^2$ and $R^3$ are each hydrogen or a branched or straight chain $C_{1-10}$-alkyl, or together with the nitrogen to which they are attached, form a 5 to 7 membered saturated or partially saturated ring, that can contain a further nitrogen atom and that can be substituted by $C_{1-3}$-alkyl.

The compounds of formula I are present as mixtures of the optically active isomers. The invention consequently is not limited just to the isomeric mixture but also includes each individual isomer of the compounds of the invention.

The compounds of the invention of formula I, can be prepared,

A) by reacting an acid of general formula II

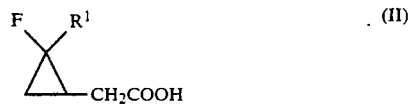

in which
$R^1$ has the meaning given in formula I, with an amide of general formula III

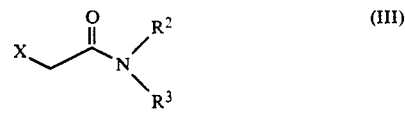

in which
$R^2$ and $R^3$ have the meanings given in formula I, and X is chloro, bromo or hydroxy, optionally in a solvent and in the presence of an acid acceptor or dehydrating agent, or B) by reacting 3-butenoic acid of general formula IV

with an amide of general formula III, optionally in a solvent and in the presence of an acid acceptor or dehydrating agent, to give an intermediate of general formula V

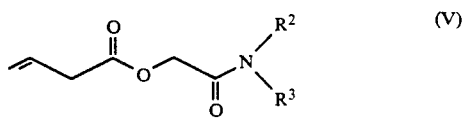

in which
$R^2$ and $R^3$ have the meanings given in formula I, and reacting this with halocarbene, in an inert solvent.

The acid of formula II and the butenoic acid of formula IV, as well as the amide of formulae III, are known or can be prepared by known methods.

Conventional basic materials are suitable as acid acceptors for reaction variants A) and B), especially aliphatic, aromatic and heterocyclic amines, such as e.g. triethylamine, dimethylaniline, dimethylbenzylamine, pyridine and dimethylaminopyridine or inorganic bases such as oxides, carbonates, hydrogen carbonates and alcoholates of alkali- and alkaline earth metals, such as potassium hydroxide, sodium hydroxide, sodium and potassium carbonate.

Suitable solvents are the previously named acid acceptors themselves or inert solvents or mixtures of these. Examples include aliphatic, alicyclic and aromatic hydrocarbons which can optionally be chlorinated, such as hexane, cyclohexane, petroleum ether, benzene, toluene, xylene, dichloromethane, chloroform, carbon tetrachloride, 1,2-dichloroethane, trichloroethylene and chlorobenzene; ethers, such as diethyl ether, methyl ethyl ether, diisopropyl ether, dibutyl ether, propylene oxide, dioxane and tetrahydrofuran; ketones, such as acetone, methyl ethyl ketone, methyl isopropyl ketone and methyl isobutyl ketone; nitriles, such as acetonitrile, propionitrile and benzonitrile; esters, such as ethyl acetate and amyl acetate; amides, such as dimethylformamide and dimethyl-acetamide; as well as sulphones and sulphoxides, such as dimethyl sulphoxide and sulpholane.

The reaction can be carried out within a wide temperature range. In general it is carried out at a temperature between $-20°$ C. and $200°$ C.

The reaction can be carried out at normal pressure, or even at higher or reduced pressure.

The production of chlorofluorocarbene can be carried out according to well known methods (eg Walselman et al. Synthesis 1985, 754). It is preferably prepared from salts of dichlorofluoroacetic in high boiling solvents such as diglyme, triglyme and tetraglyme.

Suitable chlorofluorocarbene generators are for example halofluorohydrocarbons, such as dichlorofluoromethane and alkali metal dichlorofluoroacetates, such as sodium dichlorofluoroacetate.

The production of difluorocarbene can be carried out according to well known methods in the technical literature (eg Burton and Hahnfeld, Fluorine Chem. Rev. 8 (1977), 119 ff).

Suitable substances for generating difluorcarbene are for example alkali metal chlorodifluoroacetates, such as sodium chlorodifluoroacetate; halodifluorohydrocarbons, such as chlorodifluoromethane; organo tin compounds, such as trimethyl(trifluoromethyl)tin; organo mercury compounds, such as bis(trifluoromethyl)mercury; and organo phosphorus compounds such tris(trifluoromethyl)-difluorophosphorane and triphenyl(-bromodifluoromethyl)-phosphonium bromide.

The preparation of the optical isomers of the invention can be carried out in conventional manner, for example by treatment of compounds of formula II with a chiral reagent, such as eg an optically active amine or an optically active alcohol and separation of the diastereomers so obtained by physical methods (Tetrahedron 33, 2725 (1977)), such as eg, recrystallisation, distillation or flash chromatography.

Further, the mixtures of optical isomers of general formula I, obtained from the synthesis can be separated into the enantiomers by chromatography on chiral stationary phases, such as eg cyclodextrins, starch or optically active amino acids bound to polymers (Angew. Chem. 92, 14 (1980)).

The compounds of the invention prepared by the above described processes can be isolated from the reaction mixture in conventional manner, for example by distillation of the solvent used, at normal or reduced pressure, by precipitation with water or by extraction.

A higher degree of purity can be achieved as general rule by thin layer chromatography purification, by fractional distillation or recrystallisation.

The compounds of the invention are, as a rule, almost colourless and odourless viscous oils or crystals that are almost insoluble in water, have limited solubility in aliphatic hydrocarbons, such as petroleum ether, hexane, pentane and cyclohexane, and highly soluble in chlorinated hydrocarbons, such as chloroform, methylene dichloride and carbon tetrachloride, aromatic hydrocarbons such as benzene, toluene and xylene, ethers, such as diethyl ether, tetrahydrofuran and dioxane, nitriles, such as acetonitrile, alcohols, such as methanol and ethanol, amides, such as dimethylformamide, and sulphoxides, such as dimethyl sulphoxide.

The compounds of the invention are distinguished by good insecticidal activity and especially good acaricidal activity and thus represent a valuable improvement in the state of the art. Based on their activity against a wide range of sucking arthropods, the compounds of the invention can be used not only against pests in crops but also for combating human and domestic animal parasites. The activity of the compounds of the invention is of particular importance against parasites which have developed resistance to other substances.

Examples of insects and mites, including animal ectoparasites, that can be combated by the compounds of the invention include Lepidoptera, such as *Plutella xylostella, Spodoptera littoralis, Heliothis armigera* and *Pieris brassicae*; Diptera, such as *Musca domestica, Ceratitis capitata, Erioischia brassicae, Lucilia sericata* and *Aedes aeqypti*; Homoptera, including aphids such as *Megoura viciae* and *Nilaparvata lugens*; Coleoptera, such as *Phaedon cochleariae, Anthonomus grandis, Epilachna varivestis* and corn rootworms (*Diabrotica* spp. eg. *Diabrotica undecimpunctata*); Orthoptera, such as *Blattella germanica*; ticks, such as *Boophilus microplus* and lice, such as *Damalinia bovis* and *Linognathus vituli*, as well as spider mites such as *Tetranychus urticae* and *Panonychus ulmi*, and rust mites, such as *Phyllocoptruta oleivora*.

The compounds according to the invention can be used at a concentration of 0.0005 to 5%, preferably from 0.001 to 0.1%, calculated as gram active material per 100 ml of the composition.

The compounds of the invention can be used either alone or in mixture with each other or another insecticide. Optionally other plant protection or pesticides, such as for example insecticides, acaricides or fungicides can be added depending on the desired result.

An improvement in the intensity and speed of action can be obtained, for example, by addition of suitable adjuvants, such as organic solvents, wetting agents and oils. Such additives may allow a decrease in the dose.

Suitable mixture partners may also include phospholipids, e.g. such as from the group phosphatidylcholine, hydrogenated phosphatidylcholine, phosphatidylethanolamine, N-acyl-phosphatidylethanolamine, phosphatidylinositol, phosphatidylserine, lysolecithin or phosphatidylglycerol.

The designated active ingredients or their mixtures can suitably be used, for example, as powders, dusts, granules, solutions, emulsions or suspensions, with the addition of liquid and/or solid carriers and/or diluents and, optionally, binding, wetting, emulsifying and/or dispersing adjuvants.

Suitable liquid carriers are, for example aliphatic and aromatic hydrocarbons such as benzene, toluene, xylene, cyclohexanone, isophorone, dimethyl sulphoxide, dimathylformamide, other mineral-oil fractions and plant oils.

Suitable solid carriers include mineral earths, e.g. tonsil, silica gel, talcum, kaolin, attapulgite, limestone, silicic acid and plant products, e.g. flours.

As surface-active agents there can be used for example calcium lignosulphonate, polyoxyethylenealkylphenyl ether, naphthalenesulphonic acids and their salts, phenolsulphonic acids and their salts, formaldehyde condensates, fatty alcohol sulphates, as well as substituted benzenesulphonic acids and their salts.

The percentage of the active ingredient(s) in the various preparations can vary within wide limits. For example, the compositions can contain about 10 to 90 percent by weight active ingredients, and about 90 to 10 percent by weight liquid or solid carriers, as well as, optionally up to 20 percent by weight of surfactant.

The agents can be applied in customary fashion, for example with water as the carrier in spray mixture volumes of approximately 100 to 3,000 l/ha. The agents can be applied using low-volume or ultra-low-volume techniques or in the form of so-called microgranules.

Formulations can be prepared, for example, from the following ingredients.

A

WETTABLE POWDER 20 percent by weight active ingredient
35 percent by weight bentonite
8 percent by weight calcium lignosulphonate
2 percent by weight of the sodium salt of N-methyl-N-oleyltaurine
35 percent by weight silicic acid

B

PASTE 45 percent by weight active ingredient
5 percent by weight sodium aluminium silicate
15 percent by weight cetylpolyglycol ether with 8 moles ethylene oxide
2 percent by weight spindle oil
10 percent by weight polyethylene glycol
23 parts water

C

EMULSIFIABLE CONCENTRATE 20 percent by weight active ingredient
75 percent by weight isophorone
5 percent by weight of a mixture based on the sodium salt of N-methyl-N-oleyltaurine and calcium lignosulphonate The following Examples illustrate the preparation of compounds of the invention.

EXAMPLE 1

N-{[2-(2,2-Difluorocyclopropyl)acetoxy]acetyl}pyrrolidine

A solution of 2.72 g (0.02 mol) 2,2-difluorocyclopropyl-acetic acid and 3.84 g (0.02 mol) N-(bromoacetyl)-pyrrolidine in 10 ml dimethylformamide was treated, at room temperature, with 0.3 g sodium iodide and 2.8 ml (0.02 ml) triethylamine and the mixture stirred at room temperature for 10 hours. It was then poured into water and extracted three times with ethyl acetate. The combined ethyl acetate phases were washed with first with aqueous 2% sodium hydrogen carbonate and then with water, dried over magnesium sulphate and concentrated. The crude product was purified by silica gel column chromatography using hexane/ethyl acetate (1:1) as eluent. A sample was analysed by thin layer chromatography using hexane/ethyl acetate (1:1) as eluent ($R_f$:0.18). 3.3 g (66% of theory) of product was obtained.

$n^{20}_D$ 1.4669

In a similar manner, the following compounds were prepared.

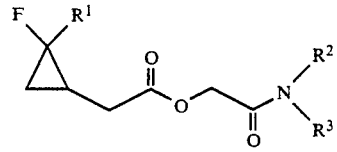

| Example | $R^1$ | $R^2$ | $R^3$ | $n_D^{20}$ | mp(°C.) |
|---|---|---|---|---|---|
| 2 | F | —CH$_2$—CH$_2$—CH$_2$—CH$_2$—CH$_2$— | | | 60–61 |
| 3 | F | C$_4$H$_9$ | C$_4$H$_9$ | 1.4488 | |
| 4 | F | C$_2$H$_5$ | C$_2$H$_5$ | 1.4445 | |
| 5 | F | CH(CH$_3$)$_2$ | CH(CH$_3$)$_2$ | | 74 |
| 6 | F | C$_6$H$_{13}$ | C$_6$H$_{13}$ | 1.4512 | |
| 7 | Cl | CH(CH$_3$)$_2$ | CH(CH$_3$)$_2$ | | 50 |
| 8 | F | —CH$_2$CH$_2$N(CH$_3$)—CH$_2$CH$_2$— | | 1.4747 | |
| 9 | F | —CH$_2$CH(CH$_3$)CH$_2$CH(CH$_3$)CH$_2$— | | | 83.1 |
| 10 | F | —CH$_2$C(CH$_3$)$_2$CH$_2$CH(CH$_3$)CH$_2$CH$_2$— | | 1.4702 | |
| 11 | F | —CH$_2$CH=CHCH$_2$CH$_2$— | | 1.4798 | |
| 12 | F | —CH$_2$CH$_2$CH$_2$CH$_2$CH$_2$CH$_2$— | | 1.4765 | |
| 13 | F | CH(CH$_3$)$_2$ | H | 1.4417 | |
| 14 | F | C$_6$H$_{11}$ | H | 1.4438 | |

The following Example illustrate the activity of the compounds of the invention

USE EXAMPLE A

Activity in the prophylactic treatment of feed against the against black bean aphids (*Aphis fabae* Scop.)

From the primary leaf of field beans (*Phaseolus vulgaris nanus* Aschers.), 24 mm diameter discs were cut and either untreated or treated with a 0.1% aqueous preparations of compounds of the invention and placed on filter papers with the underside of the leaves turned upwards. After drying the test pieces, they were each infested with wingless stages of *Aphis fabae* (approx 100 per leaf piece). The experiment was replicated 3 times. The leaves were kept on wet filter papers for 2 days at 25° C. and 16 hours light per day. The percentage mortality was then estimated and the activity calculated using Abbott's method in comparison with the untreated controls.

The compounds of Examples 4–12 had an activity of 80% or more.

USE EXAMPLE B

Activity in prophylactic treatment of leaves against brown rice-hoppers (*Nilaparvata lugens* Stal)

Rice seedlings (*Oryzae sativa* L.) in the two leaf stage (about 10 per polystyrene pot of size 6.5×6.5 cm) were either untreated or dipped until dripping wet, with an aqueous preparation containing 0.1% of active material. After drying the sprayed leaves, a polystyrene cylinder was placed over each pot and through an opening, about 30 *Nilaparvata lugens* in the 4–5 stage, anaesthetised with carbon dioxide, were introduced into each pot. After closing the opening with a fine mesh screen, the pots were kept for 2 days at 28° C. and 16 hours/day of light in the glasshouse, the amount of dead hoppers was determined. The percentage mortality was then estimated and the activity calculated using Abbott's method in comparison with the untreated controls.

The compounds of Examples 1 to 3, 7, 9, 11 and 12 showed an activity of 80% or more.

USE EXAMPLE C

Activity in the prophylactic treatment of feed against the two spotted mite (*Tetranychus urticae* Koch)

From the primary leaf of field beans (*Phaseolus vulgaris nanus* Aschers.) 14 mm diameter discs were cut. Some of these were treated with a 0.1% aqueous preparations of compounds of the invention and these along side untreated discs were placed on filter papers with the underside of the leaves turned upwards. After drying the test pieces, they were each infested with six adult female *Tetranychus urticae* and maintained for 3 days at 25° C. and 16 hours light per day. The experiment was replicated 4 times. Dead and alive adults were then counted and removed. Similarly the number of eggs laid were counted. After a further 7 days, the number of living larvae were counted, the activity calculated using Abbott's method in comparison with the untreated controls.

The compounds of Examples 1 to 14 had 80–100% activity.

USE EXAMPLE D

Activity in the curative treatment against eggs of the two spotted mite (*Tetranychus urticae* Koch)

From the developed primary leaf of field beans (*Phaseolus vulgaris nanus* Aschers.) 14 mm diameter discs were cut and layed with the upper surface face down on wet filter paper. Each disc was infested with at least 5 adult female Tetranychus urticae and maintained for 2 days at around 25° C., 50–60% relative humidity and 16 hours light per day. After collecting the adults, the leaf discs with the laid eggs were dipped in a preparation containing 0.0064% of active ingredient and surfactant. As a control, leaf discs were dipped in water containing surfactant in the same concentration as in the preparations containing active ingredient. After counting the eggs, the leaf discs were maintained for 7 days at around 25° C., 50–60% relative humidity and 16 hours light per day. From the percentage difference of laid eggs and living larvae in comparison with the controls, the activity was calculated using Abbott's method. The average of three replicates was recorded.

An activity of 80% or more was shown by the compounds of Examples 1 to 3.

USE EXAMPLE E

Insecticidal activity against sheep blowfly (*Lucilia sericata*)

1 ml Aliquots of an acetone solution containing test compound at various concentrations were applied to cotton wool dental rolls 1 cm×2 cm, contained in glass vials (2 cm diameter×5 cm long). After drying, the treated materials were then impregnated with 1 ml of nutrient solution, infested with first instar larvae of sheep blowfly (*Lucilia sericata*), closed by a cotton wool plug and held at 25° C. for 24 hours.

For the controls the mortality was <5% whereas the compounds of Examples 8, 11 and 14 an $LC_{50}$ of 300 ppm or less.

USE EXAMPLE F

Activity against tick larvae (*Boophilus microplus*)

Filter papers (9 cm in diameter) were impregnated with 1 ml aliquots of acetone solutions of test compound at various concentrations. The papers were allowed to dry and then folded into envelopes in which cattle tick larvae, (*Boophilus microplus*) were enclosed and held at 25° C. and 80% R.H. for 48 hours. The percentage mortality of tick larvae was then recorded and compared with controls.

The controls gave a mortality of less than 5% whereas the compound of Examples 12 caused 50% mortality at a concentration of 300 ppm or less.

USE EXAMPLE G

Activity against gravid female ticks (*Boophilus microplus*) - Paquera strain)

Groups of 5 mature female cattle ticks were dipped for 10 minutes in aqueous-acetone solvent dispersions of test compound containing a wetting agent, dried and then placed in individually compartmented plastic containers held at 25° C. and >80% R.H., until mortality of ticks or fecundity and viability of eggs produced by survivors could be assessed. The percentage reduction in total reproductive capacity (i.e. the combined effects of adult mortality, reduced fecundity and mortality of eggs) was then recorded and compared with controls. The controls gave less than 5% reduction of reproductive capacity whereas compounds of Examples 1–3 gave at least 50% reductions of reproductive capacity at a concentration of 500 mg/liter or less.

We claim:

1. 2-Fluorocyclopropylacetic acid ester of formula I

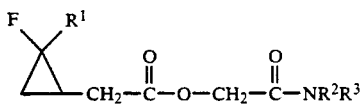

in which
R¹ is hydrogen, fluorine or chlorine, and
R² and R³ together with the nitrogen to which they are attached form a saturated, partially saturated or unsaturated 5 membered heterocyclic ring containing 1 or 2 nitrogen atoms and which is optionally substituted by $C_{1-3}$ alkyl.

2. 2-Fluorocyclopropylacetic acid ester according to claim 7, in which R² and R³ together with the nitrogen to which they are attached form a 5 membered saturated or partially saturated heterocyclic ring, containing 1 or 2 nitrogen atoms and that can be substituted by $C_{1-3}$-alkyl.

3. 2-Fluorocyclopropylacetic acid ester according to claim 2 in which R¹ is fluorine or chlorine.

4. 2-Fluorocyclopropylacetic acid ester according to claim 3 in which R² and R³ together with the nitrogen to which they are attached form a pyrrolidino group.

5. An insecticidal and acaricidal composition which comprises a compound claimed in claim 3, in admixture with an agriculturally acceptable diluent or carrier.

6. An insecticidal and acaricidal composition which comprises a compound claimed in claim 4, in admixture with an agriculturally acceptable diluent or carrier.

7. An insecticidal and acaricidal composition which comprises a compound claimed in claim 1, in admixture with an agriculturally acceptable diluent or carrier.

8. A method of combating insects and acarids which comprises applying to the insects or acarids or their locus an effective amount of a compound claimed in claim 1.

9. A method of combating insects and acarids which comprises applying to the insects or acarids or their locus an effective amount of a compound claimed in claim 3.

10. A method of combating insects and acarids which comprises applying to the insects or acarids or their locus an effective amount of a compound claimed in claim 4.

11. A method of combating insects and acarids which comprises applying to the insects or acarids or their locus an effective amount of a compound claimed in claim 2.

* * * * *